(12) United States Patent
Adolph et al.

(10) Patent No.: US 6,230,545 B1
(45) Date of Patent: May 15, 2001

(54) OPTODE FOR THE DETERMINATION OF GASES

(75) Inventors: Dietrich Adolph, Albershausen; Anton Pfefferseder, Sauerlach-Arget; Andreas Hensel, Vaihingen, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/141,295

(22) Filed: Aug. 28, 1998

(30) Foreign Application Priority Data

Sep. 19, 1997 (DE) ............................................... 197 41 335

(51) Int. Cl.[7] ........................... G01N 33/84; G01N 31/22; G01N 21/17
(52) U.S. Cl. ...................... 73/31.05; 73/23.2; 422/82.06; 422/82.09; 436/167; 356/437
(58) Field of Search ................ 73/24.02, 24.06, 73/31.05, 23.2, 23.31, 23.32; 422/86, 82.06, 91, 82.09; 436/167, 169, 171; 356/437, 439

(56) References Cited

U.S. PATENT DOCUMENTS

| | | | |
|---|---|---|---|
| 4,661,320 | * | 4/1987 | Ito et al. ................................. 422/86 |
| 4,752,447 | * | 6/1988 | Kimmel et al. ......................... 422/56 |
| 4,834,497 | | 5/1989 | Angel . |
| 5,030,420 | | 7/1991 | Bacon et al. . |
| 5,037,968 | * | 8/1991 | Simon et al. ......................... 534/851 |
| 5,049,358 | * | 9/1991 | Lau ........................................ 422/56 |
| 5,086,286 | * | 2/1992 | Yasukawa et al. .................... 73/23.2 |
| 5,294,402 | * | 3/1994 | Schrepp et al. ....................... 422/57 |
| 5,300,439 | * | 4/1994 | Charlton ................................ 436/74 |
| 5,340,714 | * | 8/1994 | Katsilometes ........................... 435/6 |
| 5,394,934 | * | 3/1995 | Rein et al. ............................. 165/16 |
| 5,405,583 | * | 4/1995 | Goswami et al. ..................... 422/86 |

(List continued on next page.)

FOREIGN PATENT DOCUMENTS

| | | |
|---|---|---|
| 37 43 684 | 7/1989 | (DE) . |
| 40 33 357 | 4/1992 | (DE) . |
| 40 37 431 | 10/1992 | (DE) . |
| 34 29 562 | 3/1993 | (DE) . |
| 0 578 630 | 1/1994 | (EP) . |
| 0 737 768 | 1/1996 | (EP) . |
| 0 578 630 | 2/1996 | (EP) . |
| 0 903 573 | 8/1998 | (EP) . |

OTHER PUBLICATIONS

Klaus Steiner, "Technische Gassensoren", Technisches Messen 62 (1995) 4, p. 135*.

Josef Gerblinger und Hans Meixner, "Chemosensoren für hohe Temperaturen", Technisches Messen 62 (1995) 5, pp. 198–203*.

Gerolf Kraus et al., "Mustererkennung und Multikomponentenanalyse bei chemischen Sensoren", Technisches Messen 62 (1995) 6, pp. 229–236*.

I. Lundstrom, "Approaches and Mechanisms To Solid State Based Sensing", Sensors And Actuators B, 1996, pp. 11–19.

E.C.M. Hermans, "CO, $CO_2$, $CH_4$, And $H_2O$ Sensing By Polymer Covered Interdigitated Electrode Structures", Sensors And Actuators, 5 (1984), pp. 181–0186.

U.E. Spichiger et al., "Optical Quantification Of sodium, Potassium And Calcium Ions In Diluted Human Plasma Based On Ion–Selective Liquid–Membranes", SPIE, vol. 1510 (1991) pp. 119–130.

*Primary Examiner*—Hezron Williams
*Assistant Examiner*—Michael Cygan
(74) *Attorney, Agent, or Firm*—Kenyon & Kenyon

(57) ABSTRACT

A gas-sensitive sensor membrane for the determination of gas concentrations in gas mixtures is proposed. Also proposed are a method and an apparatus for determining gas concentrations based on the change in the electromagnetic radiation absorption properties and/or the optical refraction index of an indicator substance, contained in the sensor membrane, which interacts with the gas to be determined.

38 Claims, 3 Drawing Sheets

U.S. PATENT DOCUMENTS

Figure 1:
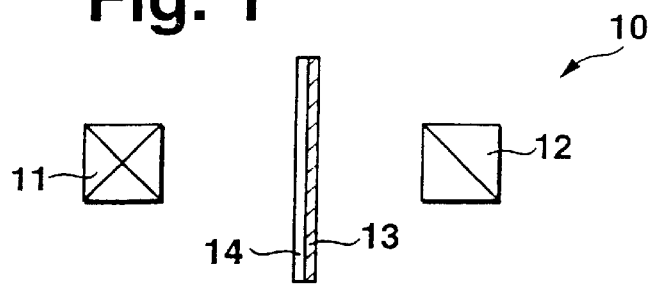

| | | | | |
|---|---|---|---|---|
| 5,460,971 | * | 10/1995 | Gottlieb | 436/68 |
| 5,494,640 | * | 2/1996 | Simon et al. | 422/82.05 |
| 5,552,765 | * | 9/1996 | Vane et al. | 340/515 |
| 5,567,622 | | 10/1996 | Jaduszliwer et al. . | |
| 5,591,581 | * | 1/1997 | Massey et al. | 435/6 |
| 5,610,393 | | 3/1997 | Klimcak et al. . | |
| 5,623,561 | * | 4/1997 | Hartman | 385/12 |
| 5,641,640 | * | 6/1997 | Hanning | 435/7.92 |
| 5,644,069 | * | 7/1997 | Liu et al. | 73/23.2 |
| 5,665,844 | * | 9/1997 | Prass et al. | 526/328 |
| 5,691,465 | * | 11/1997 | Carr et al. | 73/24.02 |
| 5,733,506 | * | 3/1998 | Silver et al. | 422/90 |
| 5,830,134 | * | 11/1998 | Caputo et al. | 422/82.09 |
| 5,979,423 | * | 11/1999 | Poindexter et al. | 123/697 |
| 5,981,467 | * | 11/1999 | Hogan, Jr. | 514/1 |

* cited by examiner

OPTODE FOR THE DETERMINATION OF GASES

BACKGROUND OF THE INVENTION

1. Field of the Invention

The present invention concerns a sensor membrane of an optode, a method for the determination of gases in gas mixtures, and an apparatus for the determination of gases in gas mixtures.

2. Description of Related Art

The increasing demand for direct, reliable, and rapid determination of gas concentrations in gas mixtures, for example in medicine, environmental engineering, smoke and fire detection, the monitoring of chemical processes, or also for measuring the exhaust gases of internal combustion engines, is leading to greater interest in the development of novel gas sensors. Only at great cost and in relatively unreliable fashion, for example, has it hitherto been possible to use electrochemical sensors based on mixed oxide materials for controlling climate control systems in automobiles (A. Zeppenfeld et al., Sensor 97 Conference Report 1, p. 113 ff.). Also known, for example, is the measurement of oxygen partial pressure in the exhaust gases of internal combustion engines by means of "lambda probes," which are also based on ceramic materials. An overview of methods for determining gases using solid electrolytes is provided by the article by I. Lundström, Sensor and Actuators B 1996, 35–36, p. 11 to p. 19, which also, in particular, discusses production, miniaturization, and cross-sensitivity problems. An attempt to eliminate, in particular, cross-sensitivities in gas determination is described in the article by E. Hermanns in Sensors and Actuators 1984, 5, pp. 181 to 186. In this context, gases are determined via the change in the electrical conductivity of polymers caused by gas absorption. The change in the layer thickness of polymer films which can absorb gases is measured by means of interference reflection (EP 0 737 768 A2). U.S. Pat. No. 5,030,420 discloses an apparatus for determining oxygen in gaseous mixtures by means of an optical sensor, also referred to as an optode, in which the quenching luminescence of ruthenium(II) complexes is measured. Another route to the determination, in particular the optical measurement, of chemical compounds and ions is offered by "ionophores." These are lipophilic ligands which have the ability selectively to complex specific ions and to transport them through membranes by means of a carrier mechanism (EP 0 578 630 B1), so that various ions are selectively determined in solution and can be detected calorimetrically. Among these ionophores, the electroneutral ionically active substances have gained particularly wide applicability as components in ion-selective liquid membrane electrodes, for example as polymer liquid membrane electrodes in clinical analysis, as microelectrodes in electrophysiology, and in high-selectivity ion transport through artificial membranes. Recently, they have also been used in optode membranes for reversible optical detection of charged and electrically neutral species in solution (U. E. Spichiger et al., Proceedings SPIE—Int. Soc. Opt. Eng. 1991, 1510, 118). Pronounced selectivit-es were obtained, in particular, for the direct determination of $H^+$, $Li^+$, $Na^+$, $K^+$, $Cs^+$, $Mg^{2+}$, $Ca^{2+}$, $Sr^{2+}$, $Ba^{2+}$, $Tl^+$, $UO_2^{2+}$, $Cl^-$, and $CO_3^{2-}$. Two possible principles were used in this context: on the one hand, only one ion-selective chromophoric or chromogenic ligand is used, which in contact with the species to be detected changes, in particular, its color. On the other hand, the combination of electroneutral ion carriers with "chromoionophores" in very thin polymer liquid membranes allows a determination of the optical activity of those cations and anions. Both principles are usable only in pH-buffered solutions. With none of these proposed solutions, however, was it possible to accomplish a simple and rapid accurate determination of gaseous species in gas mixtures, reliably and with no great need for complex equipment, while also avoiding cross-sensitivities.

SUMMARY OF THE INVENTION

The use of a sensor membrane of an optode for determination of a physical and/or chemical parameter of a sample whose absorption properties change, on the basis of an indicator substance contained in it, due to at least indirect contact with a gas and/or gas mixture makes it possible, in extremely simple fashion, to produce miniaturized gas sensors, called "optodes," using said sensor membrane. Since only the tiniest quantities of substance are required for detection, miniaturization is particularly simple. The cost factor is also decisively reduced thereby.

Because of the fact that in the method for the determination of gases and gas mixtures, the absorption properties of the indicator substance exposed at least directly to the gas mixture are measured, it is possible in very simple fashion, by means of simple optical apparatuses, to determine gases in concentrations of a few ppb up to a few % without cross-sensitivities. This was difficult to implement with the existing measurement methods, and moreover required much more complex equipment. The indicator substance used can be, for example, a chromogenic ligand which, in a physical and/or chemical interaction with the gas species to be determined, changes its absorption spectrum for electromagnetic radiation. It is also possible to use a selective ligand in conjunction with a chromoionophore.

The detection limit can be adjusted as required, in particularly advantageous and simple fashion, by varying the layer thickness and layer composition, in particular the concentration and quantities of the compounds used, since they are correlated with one another.

In an advantageous apparatus for the determination of gases in gas mixtures, in which a gas-permeable membrane is provided whose optical absorption properties change upon at least indirect contact with a gas and/or gas mixture, at least one source of electromagnetic radiation, in particular an LED, having a discrete and selectable wavelength is provided. This makes it possible to dispense with a complex device which cannot be miniaturized, for example a UV/visible or IR device. The sensor membrane having the indicator substance contained therein can thus be irradiated with a discrete, selectable wavelength which can be determined for each gas by prior calibration, so that a transmission can be measured when an absorption is present. It is moreover also possible, in very simple fashion, to combine multiple sources of electromagnetic radiation with multiple sensor membranes which are sensitive to various gases, so that multiple gases can be measured simultaneously by means of a single apparatus. It is also possible to use one source of electromagnetic radiation with multiple discrete or integrated detectors. It is also possible to use one source of electromagnetic radiation which covers the entire spectral region, in conjunction with wavelength selectors.

Further advantageous embodiments and developments of the invention are described in the dependent claims.

In a particularly advantageous development of the sensor membrane according to the invention, the latter contains an indicator substance which is effective in gas-specific fashion. As a result, cross-sensitivities such as those which occur in particular with sensors based on metal oxides and mixed oxides are prevented in very simple fashion. It is thus possible, depending on the indicator substance, to measure each volatile compound and each desired gas, for example hydrogen, oxygen, water vapor, carbon monoxide, volatile amines, etc., without having the compounds mutually block or falsify their detection.

In a further advantageous embodiment, the indicator substance is present as an ion pair, the ion pair consisting of a cationic or anionic dye molecule, for example a phenolphthalein or eosine or fluorescein derivative, and at least one counterion compensating for the electrical charge of the dye molecule. The ion pair principle used here can make it possible to convert the gas into the corresponding ion, which is charged and consequently requires a countercharge, so that this charge of the gas, now present as an ion, can be compensated for by one of the two parts of the ion pair.

It is particularly advantageous if the indicator substance contains a compound, for example a selective ligand or a metal complex, which interacts in chemically and/or physically reversible fashion with the gas to be determined. The chemical and/or physical interaction, especially when it occurs reversibly, makes it possible to retain the sensitivity of the sensor membrane for the gas being measured without change over many measurement cycles, which has an advantageous effect on service life. Examples thereof are azobenzenes, fluorinated acetophenones, open-chain ligands such as nonactin or valinomycin compounded with chromoionophores, macrocyclic N-donor transition metal complexes such as corrins, phthalocyanines, corrols, porphyrinogens, or porphyrins which are complexed with cobalt, iron, vanadium, molybdenum, and ruthenium. Derivatives of cobyric acid and complexes of Co(III) with the aforementioned N-donor ligands are particularly sensitive to $NO_x$.

Preferably this interaction between the gas to be determined and the indicator substance leads to a spectral change, i.e. to the occurrence of an at least local absorption maximum for electromagnetic radiation. The position of the absorption maximum, i.e. the wavelength at which said absorption maximum occurs, is preferably different for each gas and can lie in the visible, infrared, or some other region of the electromagnetic spectrum, although the visible region is preferred. The height of the absorption maximum is correlated with the concentration of the interacting gas, so that the concentration of the gas in the gas mixture can thus be determined very easily. The spectral position of the absorption maximum can be specifically established, over a wide range, by suitable selection of the indicator substance and of its composition.

In a further preferred embodiment, the sensor membrane contains a chemically largely inert polymer as a supporting and protective substance, thus ensuring that only the indicator substance interacts with the gas, preventing the sensor membrane which contains said inert polymer as a support substance from possibly also reacting with the gas, which would falsify the measurement results. Utilization of the specific polymer membrane, for example PVC, siloxane, etc., also leads to improved extraction and subsequent solubility of the gas through and in the membrane. In addition, the usually lipophilic chromoionophores or ligands dissolve particularly well in the membranes, which are also lipophilic. In a further preferred embodiment, the sensor membrane also contains a plasticizer, so that the membrane remains elastic particularly in terms of mechanical stresses. In a further embodiment, the sensor membrane contains a gas-specific catalyst which allows the gas to be transported to the indicator substance and allows the activation enthalpy of the specific interaction between gaseous species and indicator substance to be decreased. Utilization of a gas-specific catalyst also improves selectivity.

Since the indicator substance interacts physically and/or chemically with the gas to be determined, it is advantageously possible for the interaction to result in a change in the electromagnetic radiation absorption property of the indicator substance, said change occurring in gas-specific fashion so that cross-sensitivities during measurement are excluded.

It is advantageous, in particular, if this change leads to an at least local maximum in the electromagnetic radiation absorption of the indicator substance, which can very easily be detected.

For this, it is particularly advantageous that the indicator substance is exposed to electromagnetic radiation of a specific wavelength, since the position of the absorption maximum is specific for each gas.

In an advantageous embodiment, when the local absorption maximum is present, the electromagnetic radiation transmission of the indicator substance is measured, said transmission correlating with the concentration or partial pressure of the gas to be determined. This makes it possible, with simple means, to determine gases down to the ppb range, accurately and without cross-sensitivities.

In a further preferred embodiment, at least one detector for electromagnetic radiation, which senses the change in the optical properties of the membrane, is provided. The detector can advantageously be a photodiode, which is economical and small and can be even further miniaturized, so that globally the apparatus requires little space and can be produced with economical means.

In an advantageous embodiment, the membrane is arranged between the source of electromagnetic radiation and the detector, so that they are in a line, so that the detector can better sense transmission.

It is possible to arrange the membrane, on a support which is transparent to electromagnetic radiation of a selectable wavelength, between the source of electromagnetic radiation and the detector; but it is particularly advantageous to arrange the membrane directly on the detector or on the transmitter, thus allowing a great savings in terms of support arrangements and thereby achieving a further miniaturization and simplification of the apparatus. It is also advantageously possible to provide between the detector/transmitter and membrane a protective layer which is at least locally gas-permeable, for example by silanization.

Advantageously, this apparatus, with the membrane, detector, and source of electromagnetic radiation, is arranged in a chamber which has at least one inlet and at least one outlet for gas mixtures, so that gases can be measured continuously.

In a preferred utilization, optodes of this kind are used to investigate exhaust gases of internal combustion engines, in particular exhaust gases of motor vehicles. It is also possible, advantageously, to perform a control operation of the internal combustion engine using the measured values obtained. This makes it possible in simple fashion, particularly when ammonia-sensitive sensors are used to monitor catalytic converters for internal combustion engines, to determine wear or the aging status thereof. By determining $O_2$ oxygen, CO, $CO_2$, HC, and $NO_x$ in exhaust gases, it is also easily possible to determine the "lambda value." In conjunction with a plurality of such sensors in a vehicle with an internal combustion engine, it is possible to effect "exhaust-optimized engine management and continuous vehicle monitoring," and thereby to optimize fuel consumption and detect wear at an early stage. It is also advantageously possible to use an apparatus according to the invention for the monitoring of air quality, such as is performed, for example, to control vent flaps in motor vehicles with climate-control systems. Apparatuses according to the invention can also be controlled [sic] for ventilation and climate control in interiors. Apparatuses according to the invention can moreover be used to monitor and regulate combustion and firing systems operated with hydrocarbons, or for example to measure $NH_3$ concentration in cold storage warehouses, for cooling systems using ammonia as the coolant, or for smoke detectors. By determining fire precursor gases using individual and/or a combination of such sensors, the detection time of smoke detectors can be significantly shortened, and resistance to false alarms can be substantially enhanced.

DETAILED DESCRIPTION OF THE DRAWINGS

The apparatus according to the invention is depicted in the drawings.

Figure 2:
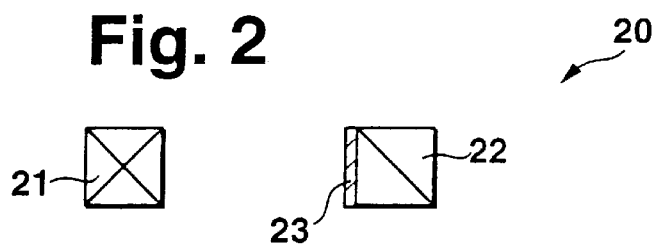
Figure 3:
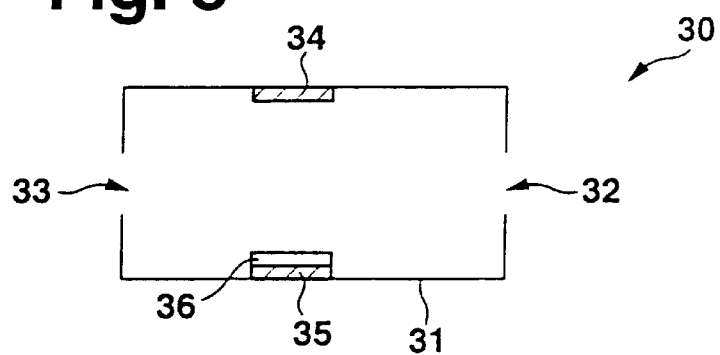
Figure 4:
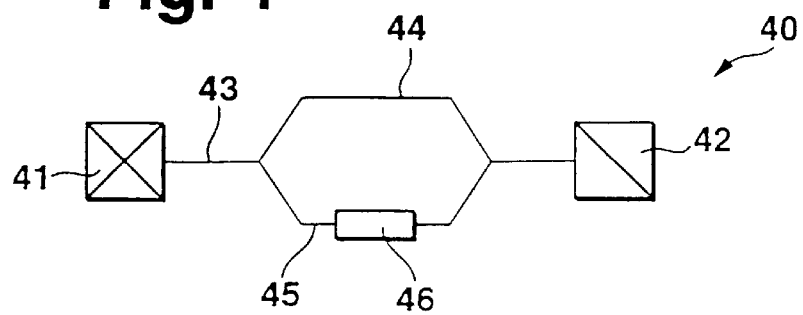
Figure 5:
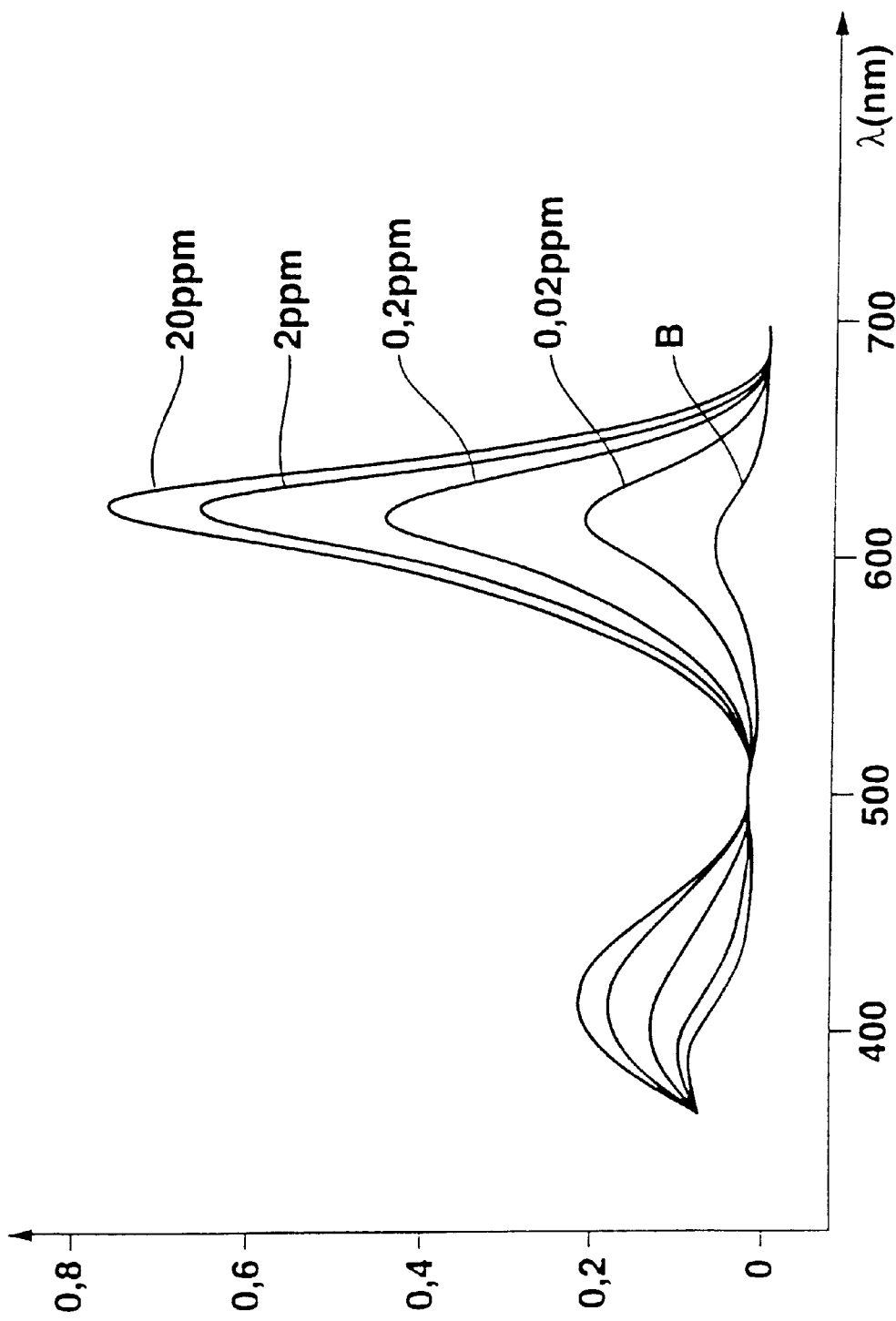
Figure 6:
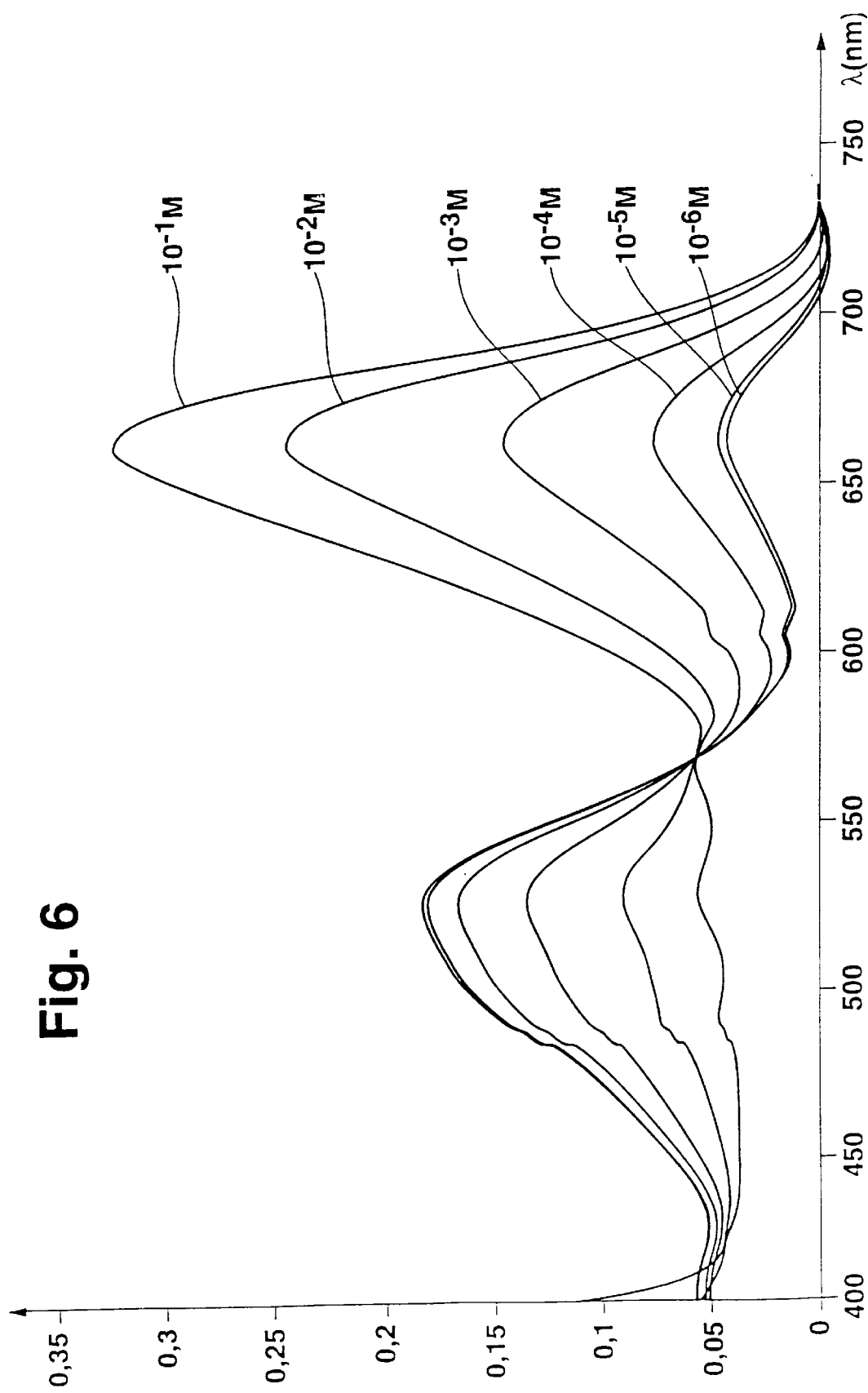

FIG. 1 shows an arrangement according to the invention for measuring gases,

FIGS. 2 to 4 show further embodiments of the apparatus according to the invention, FIG. 5 shows an absorption spectrum of an arrangement according to the invention having an $NH_3$-sensitive membrane, and FIG. 6 shows an absorption spectrum of an arrangement according to the invention having an NO-sensitive membrane; in FIGS. 5 and 6, the abscissas indicate absorption in relative units, and the ordinates indicate the wavelength in nm.

EXEMPLARY EMBODIMENTS

FIG. 1 shows the basic layout of an apparatus according to the invention. Apparatus 10 has a source 11 of electromagnetic radiation, which for example is an LED having a specific wavelength. Arranged opposite source 11 is a detector 12 for electromagnetic radiation, which for example can be a photodiode. Arranged between source 11 and detector 12, i.e. in the beam path, is a support 13 which is transparent to the radiation of source 11. It can be located exactly in the center between source 11 and detector 12, but in the context of the invention it is also possible to arrange it at any position between source 11 and detector 12, provided it is located in the beam path. A gas-permeable sensor membrane 14 according to the invention is applied on the side of support 13 facing source 11. Source 11 then emits—in continuous pulses whose duration is arbitrary, although it is preferred to select a pulse duration which is not too long—electromagnetic radiation of a wavelength which is sensed, through sensor membrane 14 and support 13, by detector 12. The sensor membrane contains an indicator substance which is sensitive to a specific gas, and has been calibrated by means of prior calibration measurements. As soon as the gas to be determined enters the space between source 11 and detector 12, the indicator substance contained in sensor membrane 14 changes its absorption for the wavelength of the electromagnetic radiation incident upon it. Since said wavelength corresponds to an at least local absorption maximum of the indicator substance, detector 12 arranged behind sensor membrane 14 and support 13 registers a change in transmission. The height of the absorption maximum, and thus the magnitude of the transmission, are proportional to the concentration of the gas, which can thus easily be sensed by an analysis arrangement (not depicted). When used in, for example, smoke detectors or the like, the analysis arrangement is additionally connected to a concentration-correlated signal generator.

FIG. 2 shows a further preferred apparatus according to the invention. Apparatus 20 is even further simplified and miniaturized as compared with FIG. 1. Also present in this case is a source 21 of electromagnetic radiation of a specific selectable wavelength, which is also emitted in pulses of selectable duration. A detector 22 for electromagnetic radiation, which has the gas-permeable sensor membrane 23 on the side facing source 21, is arranged at a spacing corresponding to the apparatus. An analysis arrangement and an optional separating layer, made for example of polysiloxane, between the sensor membrane and detector, are not depicted.

FIG. 3 shows yet another embodiment of the apparatus according to the invention. Said apparatus 30 consists of a chamber 31 which has an apparatus for gas entry 32 and an apparatus for gas discharge 33. The exact spatial arrangement of these two apparatuses is immaterial in the context of the invention. All that is important is that a source 34 of electromagnetic radiation of a discrete selectable wavelength is arranged behind gas entry 32, and a detector 35 for electromagnetic radiation, on which a gas-permeable sensor membrane 36, is arranged opposite said source 34 in the beam path. Of course it would also be possible to arrange sensor membrane 36 on a support, transparent to the selected electromagnetic radiation, between source 34 and detector 35. The detector is once again equipped with an analysis arrangement (not depicted) and an optional separating layer. The analysis arrangement can, for example, be equipped with a further device, for example to control machines and motors of any kind whose optimum operation depends on a defined gas atmosphere or a specific concentration of a gas. This is necessary, for example, in investigating the exhaust gases of motor vehicles. Because they can easily be miniaturized, the apparatuses according to the invention not only can be used in stationary units for exhaust gas investigation, but also can be installed in motor vehicles. One possibility, for example, is an ammonia-sensitive sensor membrane in an apparatus according to the invention for monitoring the status of motor vehicle catalytic converters. Measurement signals of apparatuses according to the invention which are sensitive to other gases can be utilized for engine control purposes. A further area of application consists in monitoring air quality in interiors, for example in order to control climate-control and ventilation systems.

FIG. 4 shows a further embodiment of the apparatus according to the invention. Apparatus 40 has a source 41 of electromagnetic radiation and a detector 42, for example a photodiode. Source 41 and detector 42 are connected by means of an optical fiber cable 43. The latter has a reference arm 44 and a measurement arm 45. Measurement arm 45 is in contact with sensor membrane 46, which is arranged, for example, on a support (not depicted) or on the optical fiber cable itself.

The exemplary embodiments explained, are not, of course, a limitation on the invention. It is particularly advantageous, for example, in an apparatus according to the invention, to combine multiple sensor membranes having different gas selectivities with multiple sources and detectors, or one source and a detector array for electromagnetic radiation of various wavelengths, so that multiple gas components can be determined simultaneously with a single apparatus.

Exemplary embodiments of the sensor membrane according to the invention are set forth below for various gases to be measured:

1. $NH_3$-Sensitive Sensor Membrane

Selective ligand: ETH 157 (N,N'-dibenzyl-N,N'-diphenyl-1,2-(phenylenedioxydiacetamide)); indicator: TPBE (3',3",5',5"-tetrabromophenolphthalein ethyl ester, potassium salt); plasticizer: DOS (bis-(2-ethylhexyl)-sebacate); polymer: PVC.

115 mg ETH 157 is dissolved, with 15.2 mg TPBE, 80 mg DOS, and 40 mg PVC, in 1.2 to 2 ml THF. This mixture is applied, by means of a method known per se, onto a glass plate or another suitable support. The THF solvent evaporates, and there remains behind a homogeneous, transparent gel layer which contains the active component. The gel layer is between one and four micrometers thick. Instead of ETH 157, the same molar quantity of valinomycin can also be used in this exemplary embodiment.

For calibration, a 3-micrometer thick membrane obtained in this fashion was brought into contact with several $NH_3$/air mixtures which had different $NH_3$ concentrations, and irradiated with a light source over a wide wavelength region in order to determine the position of the absorption maximum. The result is shown in FIG. 5. The absorption maximum lies at 620 nm. The curve labeled "B" represents the background signal resulting from pure air. It is clearly evident from FIG. 5 that the height of the absorption maximum is exactly correlated with the $NH_3$ concentration. The $NH_3$ concentration is indicated in ppm.

2. $CO_2$-Sensitive Sensor Membrane 2.07 mg ETH 4001 (N,N-diocytlaminophenyl-4'-trifluoroacetyl azobenzene) and 0.44 mg TDMACL (tridodecylmethylammonium chloride) are dissolved, with 80 mg pure multifunctional polysiloxane, in THF, and then applied as in the first Example onto a glass plate or another suitable support. The THF evaporates, and there remains behind a homogeneous, transparent gel layer which contains the components that are now $CO_2$-active. The thickness of the layer is between 1 and 5 micrometers.

3. $NO_x$-Sensitive Sensor Membrane 9.10 mg cyanaquacobyric acid heptacis-(2-phenylethyl ester), 3.65 mg ETH 5418 (11-[(1-butylpentyl)oxy]-11-oxoundecyl-4-{[9-(dimethylamino)-5H-benzo[a]phenoxazone-5-ylidene]amino}-benzoate) is mixed with 4.79 mg potassium tetracis-[3,5-bis(trifluoromethyl)phenyl]-borate, 80 mg DOS, and PVC in THF, and processed as in the previous Examples. The layer thickness is between 1 and 4 micrometers.

For calibration, a 3-micrometer thick membrane obtained in this fashion was brought into contact with several NO/air mixtures which had different NO concentrations, and irradiated with a light source over a wide wavelength region in order to determine the position of the absorption maximum. The result is shown in FIG. 6. The absorption maximum lies at 670 nm. It is clearly evident from FIG. 6 that the height of the absorption maximum is exactly correlated with the NO concentration. The NO concentration is indicated as a molar concentration.

These exemplary embodiments of course do not represent any limitation of the invention. According to the invention, it is equally possible to determine, using the method according to the invention, any other gas or any other compound occurring in the gaseous state, for example volatile amines, water vapor, carbon monoxide, hydrogen, oxygen, or alcohols.

What is claimed is:

1. A sensor membrane of an optode, for determination of at least one parameter of a sample of a gas or gas mixture, said parameter selected from the group consisting of chemical and physical parameters, said sensor membrane comprising an indicator substance, wherein the indicator substance changes the sensor membrane with respect to at least one property selected from the group consisting of absorption for electromagnetic radiation and optical refraction index, upon at least indirect contact with the sample of the gas or gas mixture, wherein the sensor membrane is gas-permeable, wherein the indicator substance is gas specific, wherein the indicator substance comprises at least one compound which interacts in a chemically or physically reversible fashion with a gas to be determined, and wherein the compound is selected from the group consisting of the azobenzenes, acetophenones, corrins, porphyrins, phthalocyanines, corrols, macrolides, porphyrinogens, nonactin, valinomycin, and complexes of molecules selected from the group of corrins, phthalocyanines, corrols, porphyrinogens and porphyrins with transition metals of the I–II or V–VIII subgroup.

2. The sensor membrane of claim 1, wherein the indicator substance comprises at least one compound selected from the group consisting of azobenzenes, acetophenones, macrolides, and corrins.

3. The sensor membrane as defined in claim 1, wherein the indicator substance responds to at least two gases.

4. The sensor membrane as defined in claim 1, wherein the indicator substance is present as an ion pair.

5. The sensor membrane as defined in claim 4, wherein the ion pair consists of a cationic or anionic dye molecule and at least one counterion compensating for the electrical charge of the dye molecule.

6. The sensor membrane of claim 1, wherein the gas to be detected is ammonia and the indicator is 3',3",5',5"-tetrabromophenolphthalein ethyl ester, potassium salt.

7. The sensor membrane of claim 1, wherein the gas to be detected is carbon dioxide and the indicator is N,N-dioctylaminophenyl-4'-trifluoroacetyl azobenzene.

8. The sensor membrane as defined in claim 1, wherein the interaction with the gas to be determined leads to an occurrence of an at least local absorption maximum for electromagnetic radiation.

9. The sensor membrane as defined in claim 8, wherein the position of the absorption maximum is different for each gas to be determined.

10. The sensor membrane as defined in claim 8, wherein the height of the absorption maximum is correlated with the concentration of the interacting gas to be determined.

11. The sensor membrane as defined in claim 1, wherein the sensor membrane contains a polymer which is chemically largely inert.

12. The sensor membrane as defined in claim 1, wherein the sensor membrane contains a plasticizer.

13. The sensor membrane as defined in claim 1, wherein the sensor membrane contains a gas-specific catalyst.

14. The sensor membrane as defined in claim 1, wherein the sensor membrane comprises a phase transfer catalyst.

15. A method for the determination of at least one gas in a gas mixture, wherein a change in the absorption properties and/or in the optical refraction index of an indicator substance of a gas-permeable sensor membrane exposed at least indirectly to the gas mixture to be measured, wherein the indicator substance interacts physically and/or chemically with the gas to be determined, wherein the interaction causes a change in the absorption property of the indicator substance, wherein one uses at least one compound as indicator substance that is gas specific, wherein the interaction of the indicator substance with the selected gas is chemically or physically reversible, wherein the gas-specific compound is selected from the group consisting of the azobenzenes, acetophenones, corrins, porphyrins, phthalocyanines, corrols, macrolides, porphyrinogens, nonactin, valinomycin, and complexes of molecules selected from the group of corrins, phthalocyanines, corrols, porphyrinogens and porphyrins with transition metals of the I–II or V–VIII subgroup.

16. The sensor membrane of claim 1, wherein the gas to be detected is $NO_x$ and the indicator is N,N-diocytlaminophenyl-4'-trifluoroacetyl azobenzene.

17. The method as defined in claim 15, wherein the interaction results in a change in the electromagnetic radiation absorption property of the indicator substance.

18. The method as defined in claim 17, wherein the change leads to an at least local maximum in the electromagnetic radiation absorption of the indicator substance.

19. The method as defined in claim 15, wherein the indicator substance is exposed to an electromagnetic radiation of a specific wavelength.

20. The method as defined in claim 19, wherein the wavelength corresponds to a local absorption maximum of the indicator substance.

21. The method as defined in claim 20, wherein the measured electromagnetic radiation transmission of the indicator substance is measured at the wavelength of the local absorption maximum.

22. The method as defined in claim 21, wherein the measured transmission correlates with the concentration of the gas to be determined.

23. An apparatus for the determination of at least one gas in gas mixtures, wherein at least one gas-permeable membrane at least one source of electromagnetic radiation, and at least one detector of electromagnetic radiation, are provided, wherein the membrane between the source of electromagnetic radiation and the detector of electromagnetic radiation is arranged on a support which is transparent to electromagnetic radiation of a selectable wavelength and wherein a detector measures the changes of optical properties of the membrane, wherein the membrane contains an indicator substance that is gas specific and whose optical absorption properties and/or optical refraction index change upon at least indirect contact with at least one gas in a gas mixture and wherein the indicator substance contains at least one compound that is selected from the group consisting of the azobenzenes, acetophenones, corrins, porphyrins, phthalocyanines, corrols, macrolides, porphyrinogens, nonactin, valinomycin, and complexes of molecules selected from the group of corrins, phthalocyanines, corrols, porphyrinogens and porphyrins with transition metals of the I–II or V–VIII subgroup.

24. The apparatus as defined in claim 23, wherein the detector is a photodiode.

25. An ammonia sensor using the apparatus of claim 23 to determine ammonia in a gas mixture by detecting a change in absorption properties of an indicator substance caused by the ammonia.

26. The apparatus as defined in claim 23, wherein at least one source of electromagnetic radiation of a discrete and selectable wavelength is provided.

27. A smoke detector using the apparatus of claim 23 to determine a gas in a gas mixture by detecting a change in absorption properties of an indicator substance caused by the gas.

28. The apparatus of claim 26, wherein the source of electromagnetic radiation is an LED.

29. The apparatus as defined in claim 23, wherein the molecule is selected from the group consisting of azobenzenes, acetophenones, macrolides, and corrins.

30. The apparatus as defined in claim 29, wherein the membrane is arranged on the detector and/or on the source of electromagnetic radiation.

31. The apparatus as defined in claim 23, wherein the membrane, detector, and source of electromagnetic radiation are arranged in a chamber which has at least one inlet and at least one outlet for the gas mixture.

32. The apparatus as defined in claim 23, wherein the detector is equipped with an analysis arrangement.

33. The apparatus as defined in claim 23, wherein the sensor membrane is arranged on an interferometer, in particular on an optical fiber cable.

34. A method for the investigation of exhaust gases of internal combustion engines, in particular exhaust gases of motor vehicles, comprising measuring the amount of at least one gas using the apparatus of claim 23.

35. The method as defined in claim 34, comprising a step of performing a control operation of the internal combustion system using the measured values obtained.

36. A method for the monitoring of air quality in interiors comprising a step of using the apparatus of claim 23 to determine a gas in a gas mixture by detecting a change in absorption properties of an indicator substance caused by the gas.

37. The method as defined in claim 36, comprising a step of controlling apparatuses for ventilation and climate control in interiors using the measured values obtained.

38. The method of claim 34 further comprising the steps of the monitoring and regulating of combustion and firing systems operated with hydrocarbons.

* * * * *